(12) United States Patent
Cognard

(10) Patent No.: US 8,387,818 B2
(45) Date of Patent: *Mar. 5, 2013

(54) CONTAINER FOR SUSPENDING AN INSULATING BULB

(75) Inventor: Eric Cognard, Fontenay les Louvets (FR)

(73) Assignee: ST Reproductive Technologies, LLC, Navasota, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/422,720

(22) Filed: Mar. 16, 2012

(65) Prior Publication Data

US 2012/0211498 A1 Aug. 23, 2012

Related U.S. Application Data

(63) Continuation of application No. 12/450,543, filed as application No. PCT/EP2008/053503 on Mar. 25, 2008, now Pat. No. 8,181,813.

(30) Foreign Application Priority Data

Mar. 29, 2007 (FR) ...................................... 07 54114

(51) Int. Cl.
*F17C 3/00* (2006.01)
*F17C 13/00* (2006.01)
(52) U.S. Cl. .............. 220/560.1; 220/560.04; 220/23.83
(58) Field of Classification Search ............... 220/23.83, 220/23.87, 23.89, 367.1, 560.04, 560.07–560.09, 220/560.1, 560.11, 592.27
See application file for complete search history.

(56) References Cited

U.S. PATENT DOCUMENTS

| 707,634 A * | 8/1902 | Place ......................... 220/560.1 |
| 2,900,800 A | 8/1959 | Loveday |
| 4,512,471 A | 4/1985 | Kaster et al. |
| 6,119,465 A | 9/2000 | Mullens et al. |
| 8,181,813 B2 * | 5/2012 | Cognard ..................... 220/560.1 |
| 2002/0084277 A1 | 7/2002 | Mullens et al. |

FOREIGN PATENT DOCUMENTS

| EP | 0 026 691 A1 | 4/1981 |
| FR | 2 845 973 A1 | 4/2004 |
| WO | 2006055577 A2 | 5/2006 |

OTHER PUBLICATIONS

Japanese Office Action dated Jun. 25, 2012 issued in corresponding JP Application No. 2010-500249 (5 pages).
Canadian Office Action dated May. 28, 2012 issued in corresponding CA Application No. 2,682,272 (4 pages).
Chinese Notification of Second Office Action dated May 21, 2012 issued in corresponding CN Application No. 200880010492.5 (5 pages).
Korean Office Action dated Aug. 23, 2012 issued in corresponding KR Application No. 10-2009-7020067 (4 pages).
* cited by examiner

*Primary Examiner* — Harry Grosso
(74) *Attorney, Agent, or Firm* — ST Reproductive Technologies, LLC; Ryan Christensen; Cindee R. Ewell

(57) ABSTRACT

The invention relates to a container for transporting and/or storing products, and particularly a cryostat type container, having an external packaging structure having a plurality of walls defining an internal volume within which an insulating bulb is suspended, the insulating bulb having a body formed by an outer wall and an inner wall, the inner wall defining an internal volume and the body having an opening leading into the internal volume of the insulating bulb and a cover formed from one of the plurality of walls of the external packaging structure, the cover having a tubular element capable of contacting the insulating bulb to suspend the insulating bulb within the internal volume that receives the insulating bulb, the cover also allowing passage of materials through the opening when the insulating bulb is suspended.

16 Claims, 4 Drawing Sheets

CONTAINER FOR SUSPENDING AN INSULATING BULB

This Application is a continuation of U.S. patent application Ser. No. 12/450,543 filed on Sep. 28, 2009 now U.S. Pat. No. 8,181,813 which is the United States National Stage of International PCT Application No. PCT/EP2008/053503, filed Mar. 25, 2008, which was a continuation-in-part of French Application No. 0754114, filed Mar. 29, 2007, each hereby incorporated by reference.

FIELD OF THE INVENTION

This invention relates to a transportation and/or storage device comprising a double-walled insulating bulb. The invention particularly applies to the field of the transport and/or storage of products, more specifically, but not exclusively, to that of products conserved at very low temperatures by means of a cryogenic fluid, such as liquid nitrogen.

BACKGROUND OF THE INVENTION

In the field of vessels for transporting liquidated gas, there are primarily two known techniques, that is, on the one hand, hermetically sealed vessels equipped with a system enabling the internal pressure to be controlled and, on the other hand, non-hermetic vessels to which the invention particularly relates. These non-hermetic vessels are used for the transport and/or storage of liquefied gas under atmospheric pressure, these vessels being equipped to allow the free escape of vapors with a density greater than air that are produced progressively with the reheating of the liquefied gas.

For example, a cryogenic fluid such as liquid nitrogen can be transported in a thermally insulated vessel, also called a cryostat, devoid of a system ensuring the imperviousness of the closure. However, the vessel must in return be kept in a vertical position in order to avoid accidental spillage of the liquid nitrogen. This type of vessel is, for example, very widely used for transporting biological materials requiring conservation at a very low temperature. Thus, the majority of known vessels used as a transportation device are cryostats comprising an insulting bulb consisting of two metal walls separated by the void and connected by a ring ensuring the connection between the free upper ends of each of the walls, in the area of the neck of the bulb. In these vessels, the outside metal wall of the insulating bulb thus directly constitutes the outside packing of the transportation device, which can, however, have an additional packaging structure within which is the metal cryostat.

One immediately realizes that the use of metal materials to manufacture such cryostats entails a high manufacturing cost that consequently precludes any single-use utilization. Then, for transporting products whose commercial value is sometimes low, the shipment expenses generated by the use of such cryostats as transportation devices are very significant. On the one hand, the weight of the metal cryostat contributes to increasing the cost of the transport and, on the other hand, the empty repatriation of the vessel to the original place of shipment must be organized because the expenses incurred for returning it are usually less than the purchase price of a new unit.

This consignment system is a significant constraint, particularly when it involves far-away shipments by air or when the shipper must meet strong sporadic seasonal demands subject to the biological laws, which are difficult to circumvent. This is particularly the case for the reproduction of certain animal species from frozen gametes or embryos.

Furthermore, these metal cryostats are often not very stable because they exhibit a bottom with a relatively reduced section, compared to their height. The height of the cryostats is particularly determined in relation to the pipes bearing the products that are destined to be vertically introduced in the internal volume of the vessel and that facilitate transfers between vessels.

Finally, despite the use of metal materials, the transportation devices made up of such cryostats remain particularly vulnerable to shock(s) and to falling during transport, with increased risk of deterioration due to their lack of stability. In fact, in the event of shock(s) or fall(s), the forces are, particularly in the absence of a packaging structure, directly received by the outer wall of the insulating bulb and transmitted to the ring ensuring the connection with the inner wall. Such forces often cause the connecting ring to rupture, and such a rupture of the ring laid out in the area of the neck of the bulb is fatal to the transported products because the vacuum between the walls is lost; the bulb then loses its insulation properties, no longer ensuring its conservation at low temperature. What is more, to these outside forces, stemming from the shocks or the falls sustained by the cryostat, are added other forces in the opposite direction that are transmitted to the inner wall by the content of the bulb, particularly the cryogenic fluid, such as liquid nitrogen. The combining of these forces on the inner and outer walls cause severe damage to the ring, in turn leading to the total or partial loss of the cooling cryogenic liquid due to evaporation and inevitably resulting in the loss of the transported or stored product. The resistance of the ring, which is generally made of a composite or analogous material to prevent a thermal bridge from forming, is not sufficient to sustain such forces, particularly torsion. That is the reason why numerous ruptures are noted in the area of the connecting ring that constitutes the only contact point or area between the inner and outer walls of the double wall of the bulb.

One possible solution is to pack the cryostat in a packaging structure in such a way as to try to protect it at least from direct shock(s); however, such a solution also contributes to increasing both the manufacturing and usage costs of such cryostats, and the total transported weight. Furthermore, the risk of severely damaging the connecting ring is not eliminated despite this and persists particularly in case of a severe shock or a fall because the resulting forces are directly transmitted by the packaging structure to the metal outer wall of the cryostat.

Such transportation devices or metal cryostats are thus not entirely satisfactory, particularly given their manufacturing and usage costs, their vulnerability to shock(s) and to fall(s) likely to occur during transport and also preclude a single use. The invention proposes a new design for a transportation and/or storage device making it possible to specifically remedy the abovementioned shortcomings of the state of the art.

To this end, the invention proposes a device for transporting and/or storing products, particularly of cryostat type, having an external packaging structure comprising walls defining an internal volume within which is a double-walled insulating bulb whose body is formed by an outer wall and an inner wall defining an internal volume, the bulb comprising an upper neck defining an upper filling opening, the device comprising bulb supporting means that comprise attachment means capable of engaging with the only inner wall of the bulb in order to vertically suspend the bulb by its neck in such a way that the bulb hangs freely in the empty space inside the internal volume defined by the packaging structure, with no contact between the outer wall of the bulb and the walls of the packaging structure, said device being characterized in that the means for the suspended support of the bulb consist of at least one of the walls of the packaging.

SUMMARY OF THE INVENTION

Advantageously, the transportation device comprises a double-walled glass bulb, the manufacturing cost of which is very low, in comparison with metal-walled cryostats.

It should be noted that the choice of using such a double-walled glass bulb goes against the preconceptions of persons skilled in the art who, faced with the problem of the vulnerability of cryostats to shocks, favor the development of a reinforced packaging structure for their protection and not the use of a glass bulb, the vulnerability of which they had every reason to believe would be even more critical.

Advantageously, the suspension of the bulb by its neck through attachment means capable of engaging only with the inner wall makes it possible to obtain an excellent mechanical resistance from such a double-walled glass bulb in such a way that the risks of severe damage to the bulb in case of shock(s) or fall(s) are considerably reduced.

As a result of the attachment by suspension of the bulb, the outer wall is completely free from any contact, particularly with the walls or the bottom of the packaging structure, in such a way that the risks of rupturing the neck of the bulb and losing the insulation in the event of shock(s) or fall(s) are eliminated to a great degree.

Advantageously, the use of a suspended double-walled glass bulb makes it possible to achieve a transportation device with a low manufacturing cost and low weight, capable of being used for a single usage, the packaging structure of which is, for example, made of cardboard.

In fact, the packaging structure is advantageously capable of sustaining a local indentation, without necessarily inducing contact with the bulb, inasmuch as there is an empty space forming a "buffer" between the outer wall or the bottom of the bulb and the outer packaging structure.

Furthermore, in comparison with a very rigid metal structure, such a limited deformation capacity tends to further reduce the forces transmitted to the bulb since the structure is capable of absorbing it directly, at least partially, through deformation.

As the transportation device is intended for a single use, the problem of possible deterioration of the packaging structure is then relative; clearly, what is essential is that the cryostat created by the double-walled glass bulb be intact and that the transported product be conserved.

According to the invention, the complete integration of the supporting means and attachment means with one of the walls, such as a detachable wall constituting a cover, makes it possible to further reduce the manufacturing cost of the device by reducing the number of components and to propose a single-use transportation device that is reliable and can be manufactured and used at low cost.

Advantageously, such a transportation device is more ecological than the state-of-the-art devices because it is capable of being manufactured entirely or partially from recyclable materials.

According to other characteristics of the invention:
the support wall exhibits a certain elastic deformation so as to permit, particularly in case of shock(s) or fall(s), a limited movement of the bulb within the inside packaging volume, without the outer wall of the suspended bulb coming into contact with the walls of the packaging structure;
said support wall of the bulb is capable of elastically deforming to entirely or partially absorb the mechanical forces resulting from the shock(s) received by the packaging structure, particularly if the device falls, so as to prevent or to limit the transmission of such forces to the bulb;
the support wall comprising the attachment means by suspension of the bulb is a cover of the packaging structure, which is of the polyhedral or cylindrical type;
the support wall comprises a tubular element that extends at least partially through the upper opening of the bulb and that defines an orifice leading into the internal volume of the bulb, and in which the attachment means are connected with the tubular element;
the attachment means are mounted in a movable manner between a retracted position and a locking position, wherein the device comprises a control component whose downwards vertical introduction into the orifice of the tubular element causes the displacement of the attachment means towards the locking position, the control component being capable of securing the attachment means in the locking position;
the control component has at its upper end a radial flange below which a tubular body comprising at least one hole extends vertically to allow the passage of the cryogenic fluid when filling the internal volume of the bulb;
the device comprises a closing component intended to be vertically introduced into the tubular body of the control component, so as to guarantee the integrity of the device for a single use;
the closing component comprises a flange that, in addition to the flange of the control component, is equipped on its outer vertical face with an annular locking ring that is capable of engaging with the flange of the control component whose inner vertical face comprises at least one locking detent, so as to irreversibly lock the closing component and the control component;
the device comprises means of positioning the control component capable of maintaining the central position and ensuring mechanical connection between the device and the inner wall in such a way that in case of a shock or a fall, the forces are distributed over the entire inner wall;
the device comprises absorption means capable of absorbing a cryogenic fluid, such as liquid nitrogen, and the absorption means are arranged in all or part of the internal volume of the bulb;
the absorption means constitute the means of positioning the control component.

Other characteristics and advantages of the invention are evident upon reading the following detailed description, for the understanding of which one should refer to the attached drawings.

DETAILED DESCRIPTION OF THE INVENTION

In the description and the claims, the following terms will be used in a non-limiting manner and conventionally: the terms "upper" and "lower" and the orientations "lengthwise," "vertical" and "transversal" to respectively designate the elements according to the definitions provided in the description and in relation to the trihedron (L, V, T) depicted on the figures.

Figure 1:
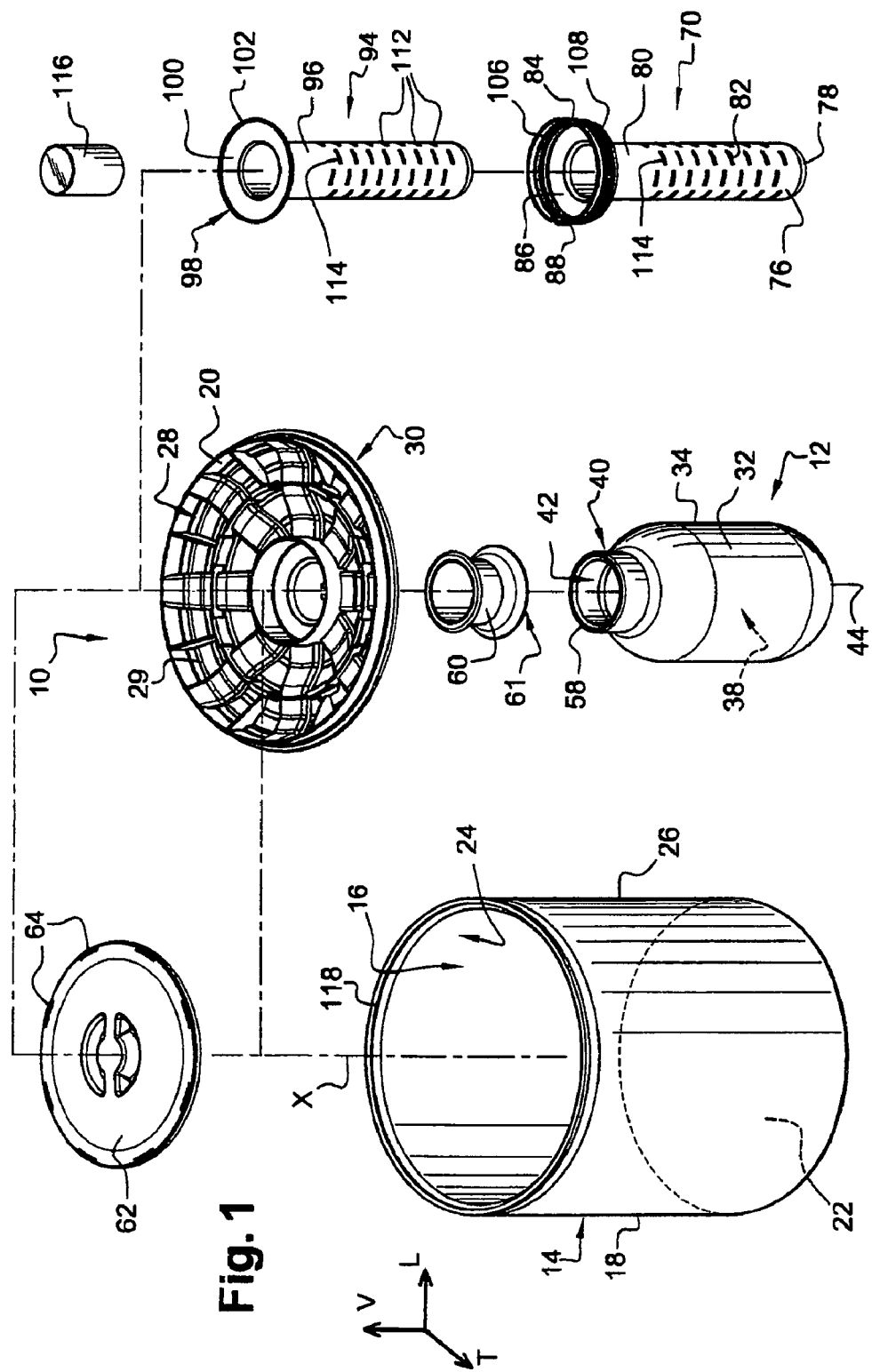
FIG. 1 is an exploded view depicting an example of execution of a transportation and/or storage device according to the invention, prior to assembly and mounting of the main components.

FIG. 1 depicts an example of execution of transportation and/or storage device 10 according to the invention. In fact, device 10 according to the invention is capable of being used as a product storage and/or transportation device, particularly conserved by means of cryogenic fluid. Advantageously, device 10 according to the invention is not exclusively intended for the transport and/or storage of biological or other products, but is also capable of being used for the transport and/or storage of cryogenic fluid itself. Advantageously, device 10 is capable of being used for either of these uses, that is to say, in order to store a product or a liquefied gas, such as a cryogenic fluid, before and/or after its transport. Transportation and/or storage device 10 primarily comprises a double-walled insulating bulb 12, advantageously made of glass, and an outer packaging structure 14.

Figure 5:
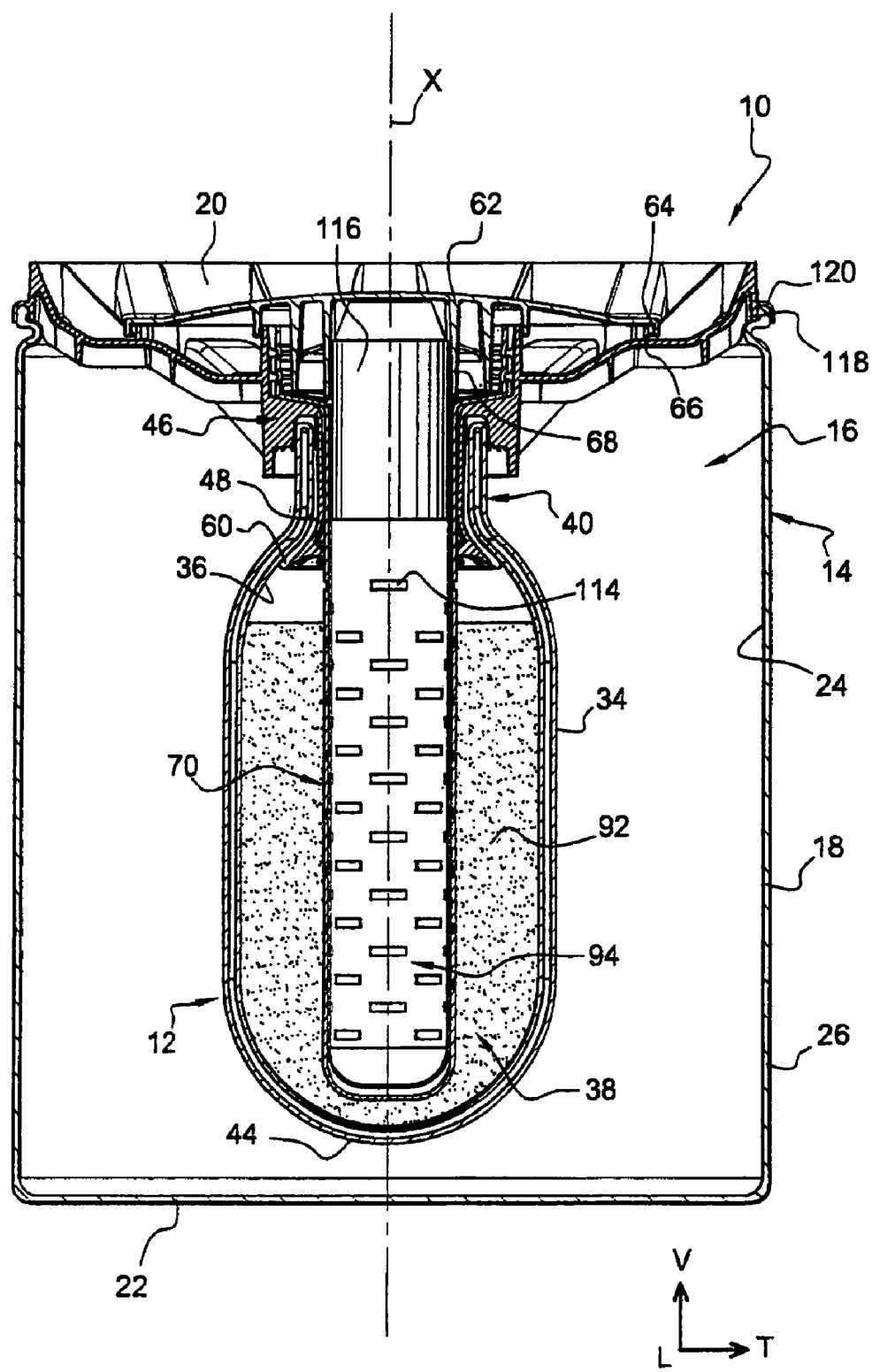
FIG. 5 is an axial cross-section depicting the transportation device of FIG. 1 in the final mounted position.

Outer packaging structure 14 consists of a set of walls defining an internal volume 16 inside which is an insulating bulb 12 arranged in the mounted position of transportation and/or storage device 10, as illustrated in FIG. 5. In the example of execution, packaging structure 14 is a container appearing in the form of a barrel, of a cask or else a drum, which is on the whole cylindrical with a circular section. Naturally, packaging structure 14 is also capable of taking very numerous forms, for example the packaging structure is, as a variant, a polyhedral type. Preferably, packaging structure 14 comprises a drum, with a main vertical axis X that has a cylindrical wall 18, an upper horizontal wall consisting of a detachable cover 20 and a lower horizontal wall 22 forming the bottom of the drum. The main vertical axis X advantageously constitutes an overall axis of symmetry for all the components of transportation and/or storage device 10. In packaging structure 14, wall 18 of the drum defines an inner cylindrical face 24 (see FIG. 5) and an outer cylindrical face 26, and circular cover 20 comprises an upper horizontal face 28 and a lower horizontal face 30.

Double-walled insulating bulb 12 comprises a body 32 consisting of an outer wall 34 and an inner wall 36, which are more or less parallel and separated by a space. Inner wall 36 defines an internal volume 38 of bulb 12 (see FIG. 5). Bulb 12 comprises an upper neck 40 defining an upper opening 42, specifically intended to permit the filling of internal volume 38 of bulb 12 with cryogenic fluid. Bulb 42 also comprises, vertically opposite neck 40, a bottom 44 that is largely hemispherical here. Advantageously, device 10 comprises supporting means 46 of bulb 12, which comprise attachment means 48 capable of engaging, directly or indirectly, with sole inner wall 36 of the bulb to vertically suspend bulb 12 by its neck 40. Thus, in a mounted position (FIG. 5) of device 10, bulb 12 hangs freely in the space within internal volume 16 defined by packaging structure 14, that is to say, without contact between outer wall 34 of bulb 12 and the walls of packaging structure 14, particularly inner wall 24 or the upper face of bottom 22. According to the invention, supporting means 46, by which bulb 12 is suspended, consist of at least one of the walls of packaging structure 14. Advantageously, supporting means 46 are directly formed by outer packaging structure 14 without the need to provide an intermediate bearing structure comprising, for example, braces.

Preferably, the wall forming supporting means 46 consists of cover 20 of packaging structure 14, detachable here and intended to be jointly added onto the cylindrical drum. Attachment means 48 by suspending bulb 12 are advantageously integrated into cover 20, so as to form a monoblock element, specifically capable of being manufactured by casting. Naturally, support wall 46 according to the invention can consist of any one of the walls of packaging structure 14, for example of any one of the walls of a box in the case of a parallelepipedic structure.

Advantageously, cover 20 forming support wall 46 according to the invention also exhibits an elastic deformation capacity determined and defined so as to permit, particularly in case of shock(s) or fall(s), a limited movement of bulb 12 in packaging internal volume 16, and in such a way that outer wall 34 of suspended bulb 12 does not contact walls 22, 24 of packaging structure 14. Preferably, cover 20 forming said wall of support 46 of bulb 12 is additionally capable of locally deforming elastically. Advantageously, cover 20 comprises an annular elastic deformation area 29 that is located on the radial periphery of cover 20. This elastic deformation area is capable of absorbing all or part of the mechanical forces resulting from shock(s) received by packaging structure 14, particularly outer wall 26 or bottom 22, in particular in the event of a vertical fall of device 10. Such an area 29 of cover 20 having a certain elastic deformation makes it possible to prevent, or at least to limit, the transmission to inner wall 36 of bulb 12 the mechanical forces attributable to such shocks onto packaging structure 14 or to a fall of transportation and/or storage device 10.

As a variant, cover 20 is made of several parts, for example a first central part on which bulb 12 is suspended, and a second less rigid peripheral part capable of deforming elastically and that, radially laid out around the central bearing part, is capable of ensuring the elastic connection with the drum of packaging structure 14. Such a second part consists, for example, of an elastic bellows, ensuring a damping and/or filtering function to limit the transmission of mechanical forces between packaging structure 14 and bulb 12.

Figure 2:
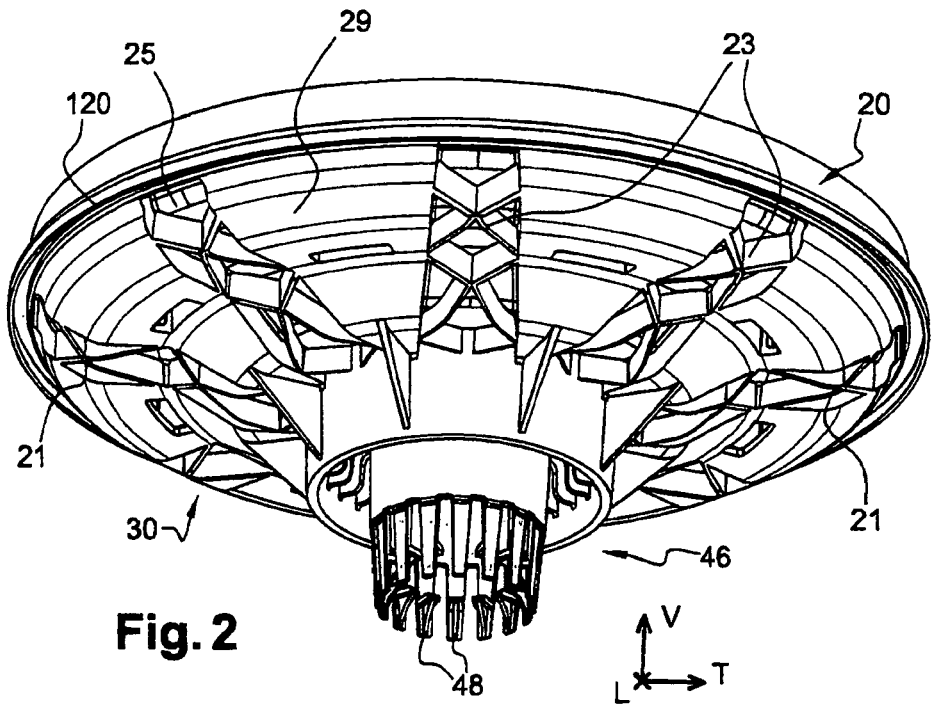
FIGS. 2 and 3 are, respectively, perspective views depicting the second in an axial cross-section through a vertical plane, the cover forming the supporting means according to the invention and that is equipped with latching tabs for suspending the bulb.
Figure 3:
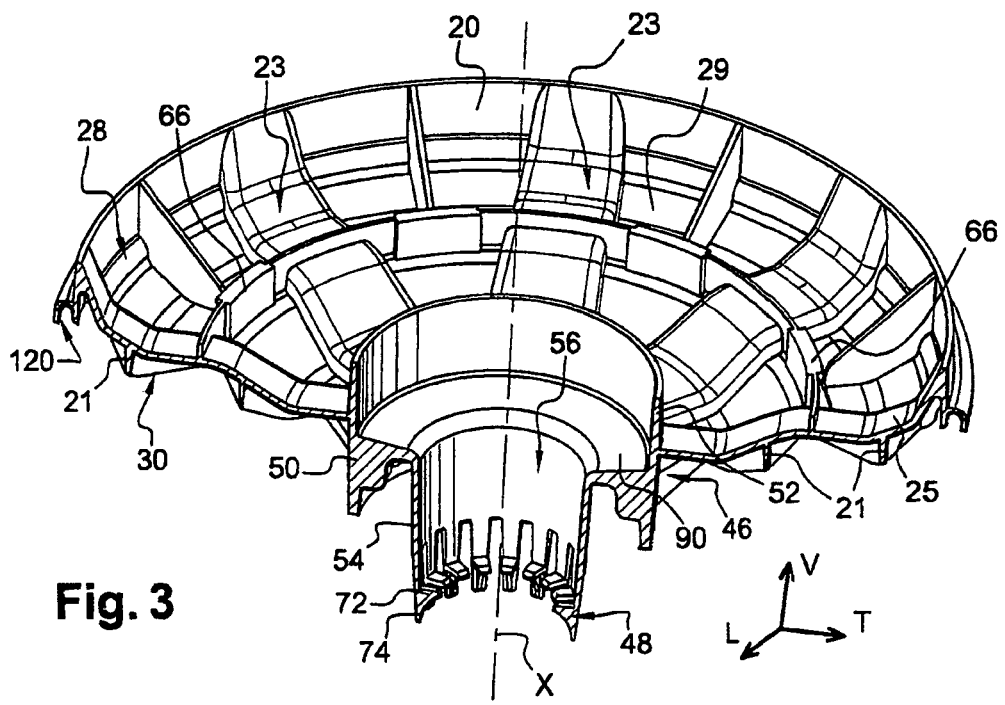

A preferred example of execution is hereafter described of a cover 20 forming support wall 46 of bulb 12 according to the invention, which is particularly illustrated in FIGS. 2 and 3. Preferably, cover 20 is made of a single piece of an elastomer material exhibiting a certain elastic deformation capacity sufficient for absorbing the forces in the event of fall or shock. Cover 20 must, however, be able to bear the weight of the assembly during transport and particularly that of bulb 12 once this is later filled with cryogenic fluid; this is the reason why the elastic deformation capacity is determined according to applications.

Consequently, the elastic deformation capacity of cover 20 is specifically a function of the weight of the bulb, of the empty space remaining around bulb 12 in volume 16, which determines the possible movement or possible displacement of bulb 12, however, without as a result permitting bulb 12 to contact structure 14.

Advantageously, cover 20 comprises reinforcement means, such as ribs 21, capable of locally rigidifying cover 20 to support the weight of suspended bulb 12 while absorbing the forces in the event of shock(s) or fall(s). Preferably, cover 20 comprises ribs 21 that are made in the shape of arms 23 extending radially from outer edge 25 towards the center of the cover and that are, for example, distributed in a "star," either angularly or regularly.

Advantageously, cover 20 incorporates supporting means 46 comprising a central tubular element 50 with a circular section here. Tubular element 50 comprises an upper block 52 and a lower block 54 that, in the mounted position, respectively extend outside and above the neck 40 of bulb 12, and at least partly through upper opening 42 of bulb 12. Central tubular element 50 defines an orifice 56 leading into internal volume 38 of bulb 12, which progressively flares out downwards from upper edge 58, which constitutes the only area of connection between the outer 34 and inner 36 walls.

Advantageously, device 10 comprises an annular sleeve 60 that, in the mounted position, is radially interposed between tubular element 50 comprising attachment means 48 and inner wall 36 of bulb 12 located in the proximity of flared neck 40 whose shape it follows.

Device 10 comprises a closing stopper 62 that is capable of obturating orifice 56 of tubular element 50 comprising cover 20. Preferably, stopper 62 is added onto cover 20 by a bayonet-type mount and includes pins 64 around its circumference intended to engage the notches 66 of cover 20. Preferably, notches 66 are distributed circumferentially around orifice 56 on upper face 28 of cover 20. Advantageously, stopper 62 comprises an annular skirt 68, which, extending vertically, is centered on the vertical axis X of device 10. Advantageously, stopper 62 is smaller in diameter than 20 and contributes, in the mounted position, to rigidifying the center part of cover 20 comprising tubular element 50 on which bulb 12 is suspended, the annular area extending radially between notches 66 and the edge of cover 20 forming said elastically deformable area 29 intended to absorb the forces in case of shocks.

Device 10 comprises a control component 70 whose vertical introduction, downwards into orifice 56 of tubular element 50, is capable of causing the movement of attachment means 48 to the locking position. Preferably, attachment means 48 consist of lugs intended, after mounting, to ensure the joint connection between bulb 12 and tubular element 50 of cover 20. Lugs 48 are mounted in a movable manner between a retracted position and a locking position and are, for example, regularly distributed circumferentially on the inside end of block 54 of tubular element 50. Each lug 48 exhibits an "L" section and includes a control arm 72 that extends horizontally, radially, inside tubular element 50, and a locking arm 74 forming a hook that extends vertically downwards, when attachment means 48 are in the retracted position as illustrated in FIG. 2 or 3. The pivoting of attachment lugs 48 from the retracted position to the locking position is accomplished by the vertical introduction downwards of control component 70, through upper orifice 56 of tubular element 50.

Control component 70 comprises a tubular body 76 of a diameter smaller than that of lower block 54 of tubular element 50 in such a way that when control component 70 is introduced axially, tubular body 76 engages with control arms 72 of lugs 48 and causes a 45° pivoting of the lugs from the retracted position to the locking position. As may better be seen on FIG. 5, tubular body 76 of control component 70 then immobilizes lugs 48 in a locking position in such a way that control component 70 advantageously constitutes a means of latching lugs 48 in the locking position. In fact, control arms 72 then extend vertically along outer cylindrical wall 80 of tubular body 76 of control component 70. Preferably, attachment lugs 48 extend obliquely in the locking position, so as to serve as a support against a face 61 opposite sleeve 60, which is integrated with inner wall 36 in the proximity of neck 40. In the mounted position, sleeve 60 is interposed radially between inner wall 36 of bulb 12 and the outside cylindrical surface of lower block 54 of tubular element 50 penetrating into bulb 12 in the area of neck 40.

As a variant, device 10 does not comprise a sleeve and lugs 48 engage directly in the locking position with the flared portion of inner wall 36 of neck 40 of bulb 12. Preferably, control component 70 comprises a tubular body 76 whose lower end 78 is closed by a bottom, in an open variant, and whose cylindrical wall 80 is equipped with at least one hole 82 to permit the passage of cryogenic fluid, specifically during filling. Advantageously, tubular body 76 comprises a plurality of holes 82 that are distributed circumferentially around cylindrical wall 80 and vertically over several superimposed rows among which holes 82 are laid out in a staggered fashion, from one row to another.

Control component 70 comprises at its upper end an upper "L" flange 84 comprising a horizontal wall 86 that extends radially to the outside from the upper end of tubular body 76 of control component 70 and a vertical wall 88. In the mounted position (FIG. 5), radial flange 84 of control component 70 is supported by means of its wall 86 against a complementary shoulder 90 formed by connecting upper block 52 and lower block 54 of tubular element 50. Preferably, control component 70 extends vertically through internal volume 38, but without direct contact between its body 76 or its end 78 and inner wall 36 of bulb 12.

Advantageously, device 10 comprises positioning means 92 that are capable of maintaining control component 70 during transport, here in the center position. Positioning means 92 particularly ensure a mechanical connection between tubular body 76 of control component 70 and inner wall 36 of bulb 12 in such a way that the forces that are capable of being transmitted in the event of a shock or fall are then advantageously distributed over the entire inner wall 36 of bulb 12 and not only on the portion of inner wall 36 in the area of neck 40 and of sleeve 60. According to a non-depicted first solution, positioning means 92 consist of a ring whose outside diameter corresponds to the inside diameter of bulb 12 and whose inside diameter corresponds to tubular body 76 of control component 70.

Advantageously, the positioning ring of component 70 is made of foam, such as a so-called filtration foam, the aerated structure of which does not or only minimally affects internal volume 38 of bulb 12. Such a positioning ring is, for example, preferred when bulb 12 of device 10 is intended to be used as a transportation and/or storage tank for a cryogenic fluid, which then directly constitutes the transported and/or stored product. According to a second solution illustrated in FIG. 5, the positioning means consist of means capable of absorbing the cryogenic fluid, liquid nitrogen, for example.

Advantageously, positioning and absorption means 92 are arranged in all or part of internal volume 38 of bulb 12, prior to introducing control component 70, and, for example, consist of polyurethane foam or phenolic foam, in flakes or expanded form. Thanks to their absorption capacity, means 92 absorb the cryogenic fluid at the time of the filling, like a liquid is absorbed by a sponge, and the fluid is subsequently no longer capable of spreading outside bulb 12 during the transport.

Advantageously, such a product transportation and/or storage device 10 is no longer affected by the regulatory restrictions imposed, particularly for air freight, on a cryostat-type container containing hazardous materials that can spill and device 10 is therefore capable of being transported like any packaging, without particular restrictions.

According to a preferred embodiment of the invention, device 10 comprises a closing component 94 that is intended to be vertically introduced into tubular body 76 of control component 70. Preferably, closing component 94 is capable of obturating holes 82 in order to limit the circulation of cryogenic fluid through control component 70 and possible contact with the transported and/or stored product. In fact, closing component 94 advantageously consists of a carrier tube inside of which is the product to be transported or stored. In a variant, the product is carried by a conventional pipe introduced inside closing component 94. Closing component 94 comprises a tubular body 96 and a flange 98 that, together with flange 84 of control component 70, primarily consists of a largely horizontal wall 100 that is equipped at its outer radial end with an annular locking ring 102. Preferably, annular locking ring 102 of flange 98 is capable of engaging with at least one locking detent 104 that comprises the internal vertical face of vertical wall 88 of flange 84 of control component 70, so as to irreversibly lock entire closing component 94 and control component 70, in order to guarantee the integrity of the single-use device, while precluding any later reuse.

Figure 4A:
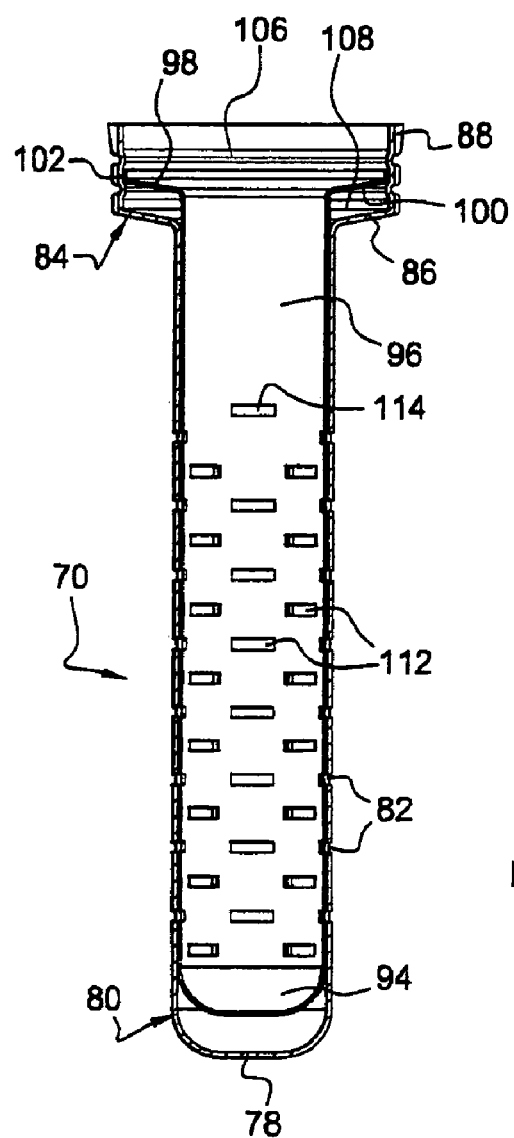
FIG. 4 is an axial cross-section respectively depicting the control and closing components of the device in the assembled position and in the locked position.
Figure 4B:
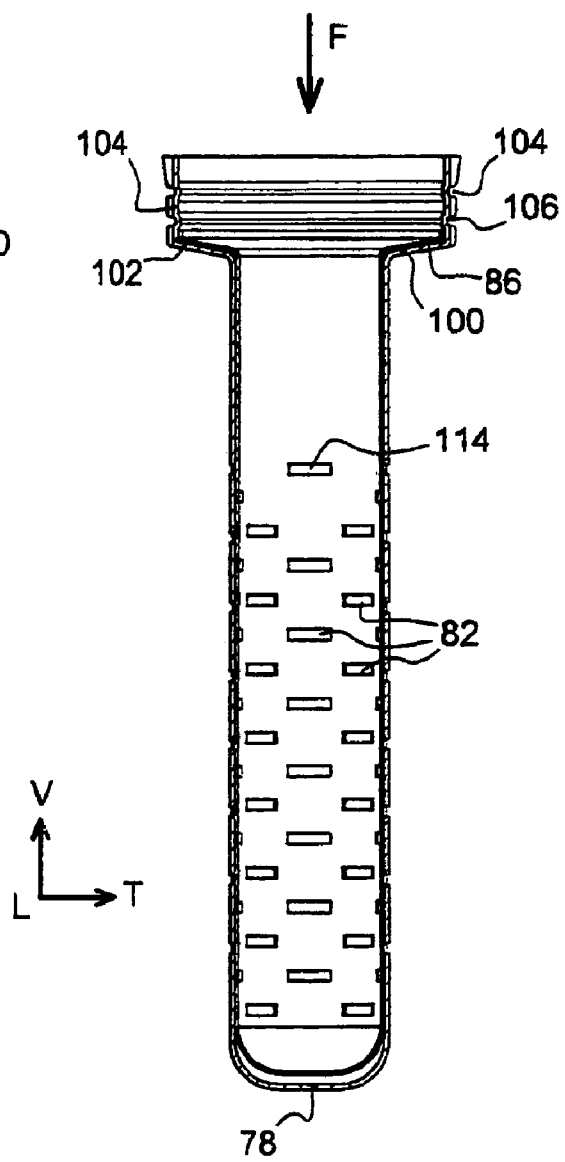

According to the example of execution illustrated in FIGS. 4A and 4B, control component 70 comprises a notched vertical face comprising at least one upper pad 106 and one lower pad 108 that respectively define a first notch 110 located between the upper and lower pads and a second notch that, located below the inside pad 108, corresponds to said notch 104. As illustrated in FIG. 4A, closing component 94 is capable of occupying a first, so-called assembly, position, in which locking ring 102 of closing component 94 is introduced into first notch 110 of flange 84 of control component 70. As illustrated in FIG. 4B, closing component 94 is still capable of occupying a second, so-called locking, position, in which ring 102 is introduced into second, so-called locking, detent 104 of control component 70.

Preferably, closing component 94 comprises holes 112 that, in assembly position, at least partly coincide with passage holes 82 of control component 70 intended to allow internal volume 38 of bulb 12 to be filled with cryogenic fluid through control component 70. Advantageously, in the locking position, holes 82 of control component 70 are at least partly obturated by body 96 of closing component 94 so as to prevent any later addition of cryogenic fluid to guarantee the end user the integrity of the device and its single-use utilization. Advantageously, absorption means 92 ensure in device 10, on the one hand, the positioning of component 70 and, on the other hand, the mechanical connection between the latter and inner wall 36 of bulb 12. Closing component 94 and control component 70 comprise ventilation means 114 intended, in the locking position, to enable the evacuation of the gases progressively released by the cryogenic fluid during transport and/or storage.

Advantageously, ventilation means 114 through closing component 94 and control component 70 consist of at least one ventilation orifice 114 that is formed by of at least one of holes 82, 112 of each component 70 and 94 located in the upper part of each of them. The upper ventilation orifices 114 permit the evacuation of gases released by the cryogenic fluid that thus escape from internal volume 38 to the outside while passing through opening 42 of neck 40 of bulb 12. The upper ventilation orifices 114 of components 70 and 94 do not coincide axially when the assembly is in the assembled position illustrated in FIG. 4A, but when components 70 and 94 are in the locked position illustrated in FIG. 4B. Preferably, the upper tubular part of closing component 94 is capable of receiving a so-called internal stopper 116, which allows the ventilation of the bulb by permitting the gases produced by the cryogenic fluid to be evacuated to the outside.

Advantageously, stopper 116 is also capable of limiting the overflow of cryogenic fluid outside bulb 12 in the event that an excessive amount was to be introduced, voluntarily or not, in relation to the maximum absorption capacity of means 92. Such a stopper 116 makes it possible, on the one hand, to limit the thermal exchanges between internal volume 38 of bulb 12 and the outside, and on the other hand, to prevent the formation of condensation in the proximity of neck 40, due to the temperature differences between the inside and the outside of the bulb.

The main stages necessary to implement transportation and/or storage device 10 in order to attain the final mounted position illustrated in FIG. 5 will now be described. Preferably, bulb 12 comprises, on the one hand, absorbing positioning means 92 that are introduced inside volume 38 and, on the other hand, sleeve 60 mounted inside neck 40. Transportation device 10 can be pre-mounted specifically by introducing tubular element 50 of the cover into upper opening 42 of bulb 12 and by proceeding with the locking. Once tubular element 50 is introduced, lugs 48 extend inside bulb 12, but are in the retracted position; it is the vertical introduction of control component 70 through passage orifice 56 of cover 20 that causes lugs 48 to pivot to their locking position. Once control component 70 is introduced, cover 20 and bulb 12 are then connected to one another through lugs 48 that are maintained in a locked position by control component 70. Preferably, control component 70 is entirely introduced into bulb 12, that is to say, until its flange 84 is received in upper block 52 of tubular element 50 and wall 86 engages with shoulder 90. Preferably, closing component 94 is mounted in control component 70 after these first assembly operations, particularly the locking of attachment means 48.

In a variant, closing component 94 is assembled with component 70 in advance, in order to be mounted simultaneously with the latter in a manner similar to that which has just been described. Preferably, cover 20 is then integrally mounted with drum 18 that includes for this purpose an upper edge 118 intended to engage with a complementary edge 120 of cover 20. Advantageously, upper edge 118 of the drum forms a male part intended to be tight-fixed into a complementary annular groove comprising edge 120 of cover 20. The engagement of forms between edges 118 and 120 of drum 18 and of cover 20 is determined in such a way that cover 20 remains connected to the drum forming outer packaging structure 14, regardless of the load exerted on it in its center by bulb 12.

Naturally, numerous variants are thus conceivable for ensuring the connection between cover 20 and upper edge 118 of the drum. Once the assembly of cover 20 with the drum of outer packaging structure 14 is completed, bulb 12 is then suspended and extends vertically into internal volume 16. Internal volume 38 of bulb 12 is then filled, through the top, by pouring the cryogenic fluid through the upper opening defined by flange 98 of closing component 94. The cryogenic fluid introduced in a certain quantity is advantageously completely absorbed by absorption means 92 provided for such purpose. Once the filling is completed, the products to be transported and/or stored are, for example, introduced directly into the volume defined by closing component 94, which then constitutes a carrier tube. In a variant, the products are carried by a support pipe (not depicted) that is vertically introduced from top to bottom inside closing component 94.

Advantageously, transportation and/or storage device 10 is capable of being closed to permit shipment of the product. Advantageously, skirt 68 of stopper 62 constitutes an actuation part capable of engaging with horizontal wall 100 of flange 98 of closing component 94 in order to cause its displacement from the assembly position to the locking position. When stopper 62 is vertically introduced downwards for the purpose of closing device 10, the lower end of skirt 68 then exercises a closing force F (FIG. 4B) on flange 98 of component 94 that causes its descent into control component 70 and the passage of locking ring 102 from first detent 110 to second detent 104. Advantageously, stopper 62 is simultaneously or successively driven in rotation by means of the handle comprising its upper face to complete the closing following the bayonet-type mounting. In fact, each notch 66 advantageously comprises a staged path (not depicted) in which each pin 64 is engaged when stopper 62 is rotated, which automatically causes a descending movement of skirt 68 when pins 64 of stopper 62 are introduced into the complementary notches 66 of support cover 20 of packaging structure 14.

Transportation and/or storage device 10 is thus capable of being transported while cover 20 on top is being maintained in the vertical position or capable of permitting the storage of the product for a period determined by the amount of cryogenic fluid. Advantageously, the use of closing component 94 or else stopper 116 in no way prevents the controlling of the transported or stored product, which can, among others, be operated by customs departments.

According to a non-depicted variant, transportation device 10 comprises only one control component 70. Control component 70 then directly constitutes a carrier tube within which the products to be transported or stored, or the support pipe containing the products are lodged. As previously, the upper part of tubular body 76 of component 70 is capable of receiving stopper 116, which permits the evacuation of the gases produced by the cryogenic fluid outside the bulb, to limit the thermal exchanges and also to limit the discharge of cryogenic fluid outside bulb 12. Thanks to the invention, transportation device 10 entails a reduced number of components, low manufacturing cost, and permits single-use utilization.

Advantageously, outer wall 34 is free from any contact and the mechanical forces transmitted in the case of shock(s) or fall(s) are only exerted on inner wall 36 alone. In fact, the mechanical forces caused by shocks or a fall are, if necessary, transmitted to inner wall 36 of bulb 12, on the one hand, by attachment means 48, which engages, directly or through the intervention of sleeve 60, with said inner wall 36 and, on the other hand, by tubular body 76 via positioning means 92, absorbent or not. Thanks to the distribution of the forces over the entire inner wall 36, the risk of rupturing neck 40 in the proximity of connection area 58 between the outer 34 and inner 36 walls of double-walled glass insulating bulb 12 in particular is eliminated.

Such a device 10 according to the invention is advantageously used for the transport and/or storage of biological products, such as gametes or embryos, but also for that of all products that must be conserved at very low temperature by a cryogenic fluid, such as liquid nitrogen, for a certain period, at least sufficient for their conveyance in the case of transport. The transported or stored products can thus also be products, such as viruses, vaccines, [and] medical samples intended to be analyzed, etc. Preferably, device 10 according to the invention is also capable of being used to perform the transport and/or storage of a cryogenic fluid, such as liquid nitrogen, the internal volume of bulb 12 in its entirety then constituting a tank for the fluid itself constituting the product.

Advantageously, device 10 does not include absorbent-type positioning means 92 when it is used as a tank for the purposes of transport or storage of such a cryogenic fluid. As long as the amount of cryogenic fluid contained in bulb 12 is sufficient to ensure the conservation of the product, device 10 is capable of being used to store it, particularly while awaiting its use.

The invention claimed is:

1. A device for transporting products comprising:
    a) an external packaging structure comprising a plurality of walls defining an internal volume that receives an insulating bulb;
    b) an insulating bulb comprising a body formed by an outer wall and an inner wall, said inner wall defining an internal volume and said body having an opening leading into said internal volume of said insulating bulb; and
    c) a cover formed from one of the plurality of walls of the external packaging structure, the cover having a tubular element capable of contacting said insulating bulb to suspend said insulating bulb within said internal volume that receives said insulating bulb, said cover allowing passage of materials through said opening when said insulating bulb is suspended.

2. The device according to claim 1 wherein the tubular element comprises a lower block that extends at least partially through said opening.

3. The device according to claim 2 wherein said lower block comprises radially arrayed lugs capable of contacting said inner wall of said insulating bulb to suspend said insulating bulb.

4. The device according to claim 3 wherein the radially arrayed lugs are movable between a retracted position and a locked position and when in the locked position, the lugs engage the inner wall of the bulb to suspend the bulb vertically within the internal volume defined by the external packaging structure with no contact between the outer wall of the bulb and the walls of the external packaging structure.

5. The device according to claim 2 further comprising a control component that when introduced into said tubular element, displaces said lower block radially outward so that said the lower block contacts said inner wall to suspend said insulating bulb within said internal volume that receives said insulating bulb.

6. The device according to claim 5 further comprising a closing component having a flange equipped on its outer vertical face with an annular locking ring capable of complimentarily engaging a flange of said control component having an inner vertical face with at least one locking detent to irreversibly lock said closing component with said control component.

7. The device according to claim 6 further comprising a positioning means capable of maintaining said control component in a center position within said internal volume of said insulating bulb and ensuring mechanical connection between said control component and said inner wall.

8. The device according to claim 7 further comprising absorption means capable of absorbing a cryogenic fluid, said absorption means located within all or a part of said internal volume of said insulating bulb.

9. The device according to claim 8 wherein said positioning means comprises an absorption means capable of absorbing a cryogenic fluid, said absorption means located within all or a part of said internal volume of said insulating bulb.

10. The device according to claim 1 wherein said cover comprises a monoblock element.

11. The device according to claim 10 wherein said monoblock element exhibits an elastic deformation capacity to limit movement of said insulating bulb in said internal volume that receives an insulating bulb.

12. The device according to claim 11 wherein said monoblock element comprises an upper horizontal face and a lower horizontal face.

13. The device according to claim 12 wherein at least a portion of the upper horizontal face comprises an exterior surface of said external packaging structure.

14. The device according to claim 1 wherein said cover comprises a detachable cover.

15. The device according to claim 1 wherein the external packaging structure comprises a cylindrical sidewall, a horizontal wall forming a bottom and said cover.

16. The device according to claim 1 wherein the cover further comprises ribs, ribs are made in the shape of arms extending radially from an outer edge of the cover towards the center of the cover.

* * * * *